(12) United States Patent
Neumann et al.

(10) Patent No.: US 11,592,399 B2
(45) Date of Patent: Feb. 28, 2023

(54) RAPID, CULTURE FREE DETECTION OF DRUG RESISTANCE CHARACTERISTICS BY RAMAN AND SURFACE ENHANCED RAMAN SPECTROSCOPIC METHODS

(71) Applicants: STC.UNM, Albuquerque, NM (US); Aaron Kurt Neumann, Albuquerque, NM (US); Anatoliy O. Pinchuk, Colorado Springs, CO (US)

(72) Inventors: Aaron Kurt Neumann, Albuquerque, NM (US); Anatoliy O Pinchuk, Colorado Springs, CO (US)

(73) Assignee: UNM Rainforest Innovations, Albuquerque, NM (US)

( * ) Notice: Subject to any disclaimer, the term of this patent is extended or adjusted under 35 U.S.C. 154(b) by 0 days.

(21) Appl. No.: 17/272,527

(22) PCT Filed: Aug. 29, 2019

(86) PCT No.: PCT/US2019/048731
§ 371 (c)(1),
(2) Date: Mar. 1, 2021

(87) PCT Pub. No.: WO2020/047202
PCT Pub. Date: Mar. 5, 2020

(65) Prior Publication Data
US 2021/0325311 A1    Oct. 21, 2021

Related U.S. Application Data

(60) Provisional application No. 62/724,094, filed on Aug. 29, 2018.

(51) Int. Cl.
| | | |
|---|---|---|
| *G01J 3/44* | (2006.01) | |
| *G01N 21/65* | (2006.01) | |
| *A61B 10/00* | (2006.01) | |

(52) U.S. Cl.
CPC ............... *G01N 21/65* (2013.01); *G01J 3/44* (2013.01); *A61B 10/00* (2013.01); *G01N 21/658* (2013.01)

(58) Field of Classification Search
CPC ......... G01N 21/65; G01N 21/658; G01J 3/44; A61B 5/0075; A61B 10/00; C12Q 1/04
See application file for complete search history.

(56) References Cited

U.S. PATENT DOCUMENTS

| | | | | |
|---|---|---|---|---|
| 5,864,397 A | * | 1/1999 | Vo-Dinh | .................. G01J 3/44 356/301 |
| 2007/0224683 A1 | * | 9/2007 | Clarke | .................. G01N 21/65 356/301 |
| 2012/0123205 A1 | * | 5/2012 | Nie | ..................... A61B 5/0075 600/109 |

* cited by examiner

*Primary Examiner* — Abdullahi Nur
(74) *Attorney, Agent, or Firm* — Gonzales Patent Services; Ellen M. Gonzales

(57) ABSTRACT

Highly sensitive assays for pathogen detection, identification and/or analysis including, but not limited to, sensing of metabolite patterns associated with high-risk drug resistance phenotypes.

9 Claims, No Drawings

US 11,592,399 B2

RAPID, CULTURE FREE DETECTION OF DRUG RESISTANCE CHARACTERISTICS BY RAMAN AND SURFACE ENHANCED RAMAN SPECTROSCOPIC METHODS

BACKGROUND

There is a clinical need for rapid diagnostics of infectious disease. The threat is particularly stark in neutropenic patients, who frequently present with systemic infections wherein every hour of delay in treatment is associated with an 18% increase in mortality (2-4). Additionally, implanted medical devices, such as central venous catheters (CVC), are now a staple of modern medicine. Five million CVCs are installed in the US annually with a high rate of dangerous device-associated infection in critically ill patients (5-8).

Candida albicans is the major human systemic fungal pathogen and, at the same time, a very common human commensal. It is the fourth most common cause of healthcare-associated bloodstream infections in the United States (1). An estimated 46,000 healthcare-associated Candida infections occur among hospitalized patients in the United States each year (2). The widespread use of antifungal drugs, such as fluconazole, has led to the development of drug resistance, which has severely hindered antifungal therapies and prompted the CDC to designate fluconazole resistant Candida as a "serious"-level drug-resistance threat (2). Bacteria and fungi readily form biofilms, which are associated with resistance to antimicrobial drugs (3-5). Biofilms are surface-associated communities of microorganisms enclosed in a matrix of extracellular polymeric substances. The process of Candida biofilm growth and dispersal, leading to dissemination of the infection from infected medical device surfaces, is regulated by microbial soluble small molecule QSMs, which are typically small organic alcohols (e.g., farnesol, tyrosol) (6, 7).

Enterobacteriaceae, such as Klebsiella pneumoniae and Escherichia coli, are among most commonly isolated pathogens in nosocomial infections (8-10). Their ability to form thick biofilms is an important virulence trait that permits them to infect surfaces of catheters and other implanted medical devices (11). These pathogens utilize gram-negative bacterial type I QSMs (acyl homoserine lactones) and type II QSMs (furanosyl borate diesters) to regulate population dynamics and biofilm production (12, 13). Carbapenem-resistant Enterobacteriaceae (CRE) are a significant and growing infectious threat in the health care setting. Some CRE pathogens are resistant to virtually all known antibiotics, and they are associated with 50% attributable mortality in cases of CRE bloodstream infection (12, 13). Therefore, the CDC has labeled CRE infection as an "urgent"-level drug resistance threat (2).

Currently, microbiological culture delays clinical diagnostic results for at least 48 hours, with additional delay for antimicrobial susceptibility testing. Therefore, empiric therapies such as broad-spectrum antibiotics are typically applied immediately until a specific pathogen is identified. These powerful drugs are lifesaving, but their use exposes patients to elevated risk of serious infectious sequelae (9, 10) and raises antimicrobial stewardship concerns due to the need to prolong the clinically useful lifetime of these drugs.

Empiric broad-spectrum antibiotic therapies decimate the patient's healthy microbiome and leave them susceptible to overgrowth by pathogens such as Candida albicans and Clostridium difficile that are normally kept in check by a healthy microbiome (14-18). Accordingly, there is a need for better-targeted therapies to be applied to patients at an earlier time such as a rapid, point of care diagnostic. Such rapid point of care diagnostics could spare patients exposure to these powerful drugs and preserve their normal microfloral populations, which are increasingly understood to be not just passive bystanders but intimately connected with health and disease on many fronts (19-24).

SUMMARY

The present disclosure provides highly sensitive assays for pathogen detection, identification and/or analysis including, but not limited to, sensing of metabolite patterns associated with high-risk drug resistance phenotypes. Such assays could be used in rapid, point-of-care diagnostics. The present disclosure also provides medical devices which are adapted for analysis via these assays.

DETAILED DESCRIPTION

The present disclosure provides highly sensitive assays and medical devices for pathogen detection, identification and/or analysis including, but not limited to sensing of metabolite patterns associated with high-risk drug resistance phenotypes. According to a specific embodiment, the present disclosure is directed towards the identification and phenotyping of a variety of pathogens including, for example, pathogens that are responsible for many bloodstream infections and biofilm-mediated contamination of indwelling medical devices, such as central venous catheters, urinary catheters and ventilator tubes (2). According to a specific embodiment, the present disclosure provides highly sensitive assays to identify microbial metabolites from a variety of pathogens including, but not necessarily limited to, fungal (e.g., Candida albicans) and gram negative bacterial (e.g., Klebsiella pneumoniae, Escherichia coli) pathogens. According to an embodiment, Raman spectroscopy and/or Surface Enhanced Raman Scattering (SERS) is used for rapid, culture-free pathogen identification and/or for sensing metabolite patterns associated with high-risk drug resistance phenotypes.

Raman spectroscopy and microscopy afford facile identification of biomolecules in complex chemical environments (22-24). Coupled with signal enhancement via plasmonic substrates, these methods can be highly sensitive (down to single molecule resolution) (25, 26). It is feasible to deploy this type of sensing technology as a point-of-care technology, as suggested by the fact that rugged, cost-effective Raman spectrometers are already used for chemical detection in security, defense and agricultural applications (27, 28). Finally, Raman imaging is non-destructive and will permit the specimen to be reused for standard, culture-based clinical microbiology, allowing the presently described approach to be a convenient, adjunctive method for detection of infectious disease that will fit within existing clinical workflows.

SERS enhances Raman scattering by detecting small molecules adsorbed or in close proximity to the surface of noble metal nanostructures (these noble metal nanostructures are generally referred to herein as "SERS sensors," or "SERS substrates"). According to an embodiment, pre-synthesized metal nanoparticles or laser-deposited metal nanostructures are used as highly efficient substrates for the sensitive detection of targeted molecules. A focused laser beam is used to deposit pre-synthesized noble mental nanoparticles in a solution or to photo-reduce ions of noble metals in a solution to atomic nano- or microstructures on a substrate. A solution of pre-synthesized metal nanoparticles or a solution of metal ions in the presence of a surfactant (e.g. silver nitrate and citrate) are used in the laser deposition process. Different morphologies and geometries of noble metal microstructures, such as dots, lines or wires, rectangular meshes and other geometries can be fabricated with a laser beam as SERS substrates. Depending on the power of the laser and exposer time micro- and nanostructures of different size between 100 nm and a few microns can be fabricated. Accordingly, noble metal nanostructures (either colloidal nanoparticles or laser-deposited nanopatterns) could be used for the detection of metabolites and Quorum Sensing Molecules (QSMs) of pathogens such as *C. albicans* and gram-negative CRE pathogens (e.g., *Klebsiella pneumoniae, Escherichia coli*) by SERS.

According to some embodiments, a laser-deposition technique could be utilized to fabricate noble metal nanostructures in, on, or in the vicinity of living cells and facilitate in situ Raman characterizations. A focused laser beam with the wavelength in UV or visible spectral range, such as a laser with the wavelength 405 nm can be used to photo-reduce metal ions from the solution to a substrate to create nanostructures of different morphology, such as dots or meshes. The present disclosure includes methods of producing plasmonic nanoparticle substrates by photoreduction of metal ions (silver or gold) inside the sample for Raman microscopy (25). These methods can be used to print SERS sensors on glass (14). Furthermore, these methods could be used to create SERS sensors directly within biofilms, where analytes are at their highest concentration (26). For example, a solution of metal ions (e.g., gold or silver) can be introduced into a biofilm and a laser beam focused inside the biofilm. Photoreduction of the metal ions into atomic micro- and nano-structures is then used to promote formation of metal nanostructures of a particular desired type within the biofilm. After laser-induced sensor deposition, the sample is scanned under confocal Raman microscopy to map the local distribution of target chemicals. This approach facilitates diagnostic readings directly on, for example, putatively pathogen-colonized medical device surfaces.

For example, a catheter or other medical device having (or suspected of having) a biofilm formed on the surface could have a SERS substrate deposited on its surface (inside the biofilm, if present) using the techniques described above. The SERS substrate (and biofilm) could then be analyzed using Raman spectroscopy for, for example, detection and/or identification of microbes. Accordingly the present disclosure contemplates a method for the formation of the SERS substrate on a medical device, a medical device having a SERS substrate formed on the surface thereof, and a method of analyzing a sample comprising collecting the Raman spectrum from the surface of a medical device, which may or may not have a SERS substrate on the surface.

Of course it will be understood that other methods for depositing or otherwise positioning a SERS sensor onto a surface are known and the present disclosure contemplates the use of such methods to place SERS sensors on the surface of medical devices for use as described herein.

As stated above, there is a need for rapid methods of diagnosing pathogen infection and characterizing the infections in, for example, a clinical environment. Accordingly, unlike methodologies that require time intensive steps like culturing of samples, the present disclosure provides culture-free classification and characterization of infectious disease from a patient specimen. According to a specific embodiment, Raman microscopy and/or SERS is used to detect biomarkers associated with the presence of pathogens having certain characteristics. For example, biomarkers associated with antibiotic resistance. Examples of suitable biomarkers include, for example, metabolic products of resistant pathogens that are detectably different from the metabolic products of susceptible strains.

In some cases, such biomarkers may not yet be identified. Accordingly, the present disclosure contemplates the use of Raman microscopy and/or SERS to identify biomarkers that are indicative of various pathogen characteristics such as, for example, drug resistance. Once identified, Raman microscopy and/or SERS can then be used, for example in a clinical setting, to rapidly characterize pathogens by detecting the presence of the previously identified biomarkers.

For example, Fluconazole inhibits 14-α-demethylase, the product of the ERG11 gene in *C. albicans* that is required to synthesize the membrane sterol ergosterol. Raman-active lipid precursors accumulate in fluconazole susceptible *C. albicans* when treated with this drug. Accordingly, SERS and Raman microscopy could be used to determine whether this signal can be detected as a biomarker of fluconazole susceptibility. Reference spectra for a variety of biomolecules relevant to the treatment of *C. albicans*, including ergosterol synthesis intermediates and other cellular lipids can be obtained for comparison. Given the complexity of spectral data in biospecimen samples, reference spectra of biomarker molecules can be used and statistical analysis applied to achieve spectral deconvolution and classification. The kinetics of changes in these biomarkers of drug susceptibility in the presence of varying fluconazole concentrations can also be observed.

As another example, CRE pathogens are very difficult to treat and require use of less common and non-preferred antibiotics due to their extensive antibiotic resistance profile. Carbapenem drug resistance in CRE pathogens typically results from expression of carbapenemases that react with and inactivate beta-lactam antibiotics, especially carbapenem class antibiotics, by cleaving their beta-lactam ring structure. Accordingly, the present disclosure provides a rapid and highly sensitive assay using SERS microscopy to detect activity of the three major classes of carbapenemases, resulting in formation of the hydrolyzed drug product by CRE *K. pneumoniae* and *E. coli* strains.

As previously noted above, Ramen spectroscopy is non-destructive and therefore permits the sample or specimen to be reused for standard, culture-based clinical microbiology testing or other purposes. Accordingly, the present disclosure contemplates a method of treatment, diagnosis, or identification wherein Raman spectroscopy and/or SERS is just one part of the tests to which a particular sample is subjected.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims.

REFERENCES

References: All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

1. Pfaller M A, Diekema D J. Epidemiology of invasive candidiasis: a persistent public health problem. Clin Microbiol Rev. 2007; 20(1):133-63. Epub 2007 Jan. 16. doi: 20/1/133 [pii] 10.1128/CMR.00029-06. PubMed PMID: 17223626; PubMed Central PMCID: PMC1797637.
2. Antibiotic resistance threats in the United States, 2013. In: (CDC) CfDCaP, editor. Atlanta, Ga. 2013.
3. Taff H T, Mitchell K F, Edward J A, Andes D R. Mechanisms of Candida biofilm drug resistance. Future microbiology. 2013; 8(10):1325-37. Epub 2013 Sep. 26. doi: 10.2217/fmb.13.101. PubMed PMID: 24059922; PubMed Central PMCID: PMC3859465.
4. Anderson G G, O'Toole G A. Innate and induced resistance mechanisms of bacterial biofilms. Current topics in microbiology and immunology. 2008; 322:85-105. Epub 2008 May 6. PubMed PMID: 18453273.
5. Kuhn D M, Ghannoum M A. Candida biofilms: antifungal resistance and emerging therapeutic options. Curr Opin Investig Drugs. 2004; 5(2):186-97. Epub 2004 Mar. 27. PubMed PMID: 15043393.
6. Mallick E M, Bennett R J. Sensing of the microbial neighborhood by Candida albicans. PLoS Pathog. 2013; 9(10):e1003661. Epub 2013 Nov. 10. doi: 10.1371/journal.ppat.1003661. PubMed PMID: 24204254; PubMed Central PMCID: PMC3814570.
7. Albuquerque P, Casadevall A. Quorum sensing in fungi—a review. Med Mycol. 2012; 50(4):337-45. Epub 2012 Jan. 25. doi: 10.3109/13693786.2011.652201. PubMed PMID: 22268493.
8. Podschun R, Ullmann U. Klebsiella spp. as nosocomial pathogens: epidemiology, taxonomy, typing methods, and pathogenicity factors. Clin Microbiol Rev. 1998; 11(4):589-603. Epub 1998 Oct. 10. PubMed PMID: 9767057; PubMed Central PMCID: PMC88898.
9. Schaberg D R, Culver D H, Gaynes R P. Major trends in the microbial etiology of nosocomial infection. Am J Med. 1991; 91(3B):72S-5S. Epub 1991 Sep. 16. PubMed PMID: 1928195.
10. de Kraker M E, Jarlier V, Monen J C, Heuer O E, van de Sande N, Grundmann H. The changing epidemiology of bacteraemias in Europe: trends from the European Antimicrobial Resistance Surveillance System. Clin Microbiol Infect. 2013; 19(9):860-8. Epub 2012 Oct. 9. doi: 10.1111/1469-0691.12028. PubMed PMID: 23039210.
11. Hall-Stoodley L, Costerton J W, Stoodley P. Bacterial biofilms: from the natural environment to infectious diseases. Nature reviews Microbiology. 2004; 2(2):95-108. Epub 2004 Mar. 26. doi: 10.1038/nrmicro821. PubMed PMID: 15040259.
12. Papenfort K, Bassler B L. Quorum sensing signal-response systems in Gram-negative bacteria. Nature reviews Microbiology. 2016; 14(9):576-88. Epub 2016 Aug. 12. doi: 10.1038/nrmicro.2016.89. PubMed PMID: 27510864; PubMed Central PMCID: PMC5056591.
13. Balestrino D, Haagensen J A, Rich C, Forestier C. Characterization of type 2 quorum sensing in Klebsiella pneumoniae and relationship with biofilm formation. J Bacteriol. 2005; 187(8):2870-80. Epub 2005 Apr. 5. doi: 10.1128/JB.187.8.2870-2880.2005. PubMed PMID: 15805533; PubMed Central PMCID: PMC1070389.
14. Leffler D A, Lamont J T. Clostridium difficile infection. The New England journal of medicine. 2015; 372(16):1539-48. Epub 2015 Apr. 16. doi: 10.1056/NEJMra1403772. PubMed PMID: 25875259.
15. Lessa F C, Mu Y, Bamberg W M, Beldays Z G, Dumyati G K, Dunn J R, et al. Burden of Clostridium difficile infection in the United States. The New England journal of medicine. 2015; 372(9):825-34. Epub 2015 Feb. 26. doi: 10.1056/NEJMoa1408913. PubMed PMID: 25714160.
16. Roy A, Chaudhuri J, Sarkar D, Ghosh P, Chakraborty S. Role of Enteric Supplementation of Probiotics on Late-onset Sepsis by Candida species in Preterm Low Birth Weight Neonates: A Randomized, Double Blind, Placebo-controlled Trial. North American journal of medical sciences. 2014; 6(1):50-7. Epub 2014 Mar. 29. doi: 10.4103/1947-2714.125870. PubMed PMID: 24678479; PubMed Central PMCID: PMC3938875.
17. Zelante T, Iannitti R G, Cunha C, De Luca A, Giovannini G, Pieraccini G, et al. Tryptophan catabolites from microbiota engage aryl hydrocarbon receptor and balance mucosal reactivity via interleukin-22. Immunity. 2013; 39(2):372-85. Epub 2013 Aug. 27. doi: 10.1016/j.immuni.2013.08.003. PubMed PMID: 23973224.
18. De Rosa F G, Corcione S, Raviolo S, Montrucchio C, Aldieri C, Pagani N, et al. Candidemia, and infections by Clostridium difficile and carbapenemase-producing Enterobacteriaceae: new enteropathogenetic opportunistic syndromes? Le infezioni in medicina: rivista periodica di eziologia, epidemiologia, diagnostica, clinica e terapia delle patologie infettive. 2015; 23(2):105-16. Epub 2015 Jun. 26. PubMed PMID: 26110290.
19. Boursi B, Mamtani R, Haynes K, Yang Y X. The effect of past antibiotic exposure on diabetes risk. European journal of endocrinology. 2015; 172(6):639-48. Epub 2015 Mar. 26. doi: 10.1530/EJE-14-1163. PubMed PMID: 25805893; PubMed Central PMCID: PMC4525475.
20. Modi S R, Collins J J, Relman D A. Antibiotics and the gut microbiota. J Clin Invest. 2014; 124(10):4212-8. Epub 2014 Oct. 2. doi: 10.1172/JCI72333. PubMed PMID: 25271726; PubMed Central PMCID: PMC4191029.
21. Cho I, Yamanishi S, Cox L, Methe B A, Zavadil J, Li K, et al. Antibiotics in early life alter the murine colonic microbiome and adiposity. Nature. 2012; 488(7413):621-6. Epub 2012 Aug. 24. doi: 10.1038/nature11400. PubMed PMID: 22914093; PubMed Central PMCID: PMC3553221.
22. Dethlefsen L, Relman D A. Incomplete recovery and individualized responses of the human distal gut microbiota to repeated antibiotic perturbation. Proc Natl Acad Sci USA. 2011; 108 Suppl 1:4554-61. Epub 2010 Sep. 18. doi: 10.1073/pnas.1000087107. PubMed PMID: 20847294; PubMed Central PMCID: PMC3063582.
23. Jernberg C, Lofmark S, Edlund C, Jansson J K. Long-term impacts of antibiotic exposure on the human intestinal microbiota. Microbiology. 2010; 156(Pt 11):3216-23. Epub 2010 Aug. 14. doi: 10.1099/mic.0.040618-0. PubMed PMID: 20705661.
24. Blaser M J, Falkow S. What are the consequences of the disappearing human microbiota? Nature reviews Microbiology. 2009; 7(12):887-94. Epub 2009 Nov. 10. doi: 10.1038/nrmicro2245. PubMed PMID: 19898491.
25. Jiang K, Spendier K, Pinchuk A O, editors. Laser-directed deposition of silver nanostructures. SPIE Nano-Science+Engineering; 2014: International Society for Optics and Photonics.
26. Ivleva N P, Wagner M, Horn H, Niessner R, Haisch C Raman microscopy and surface-enhanced Raman scattering (SERS) for in situ analysis of biofilms. Journal of biophotonics. 2010; 3(8-9):548-56. Epub 2010 Jul. 1. doi: 10.1002/jbio.201000025. PubMed PMID: 20589769.

The invention claimed is:

1. A method for detecting the presence of or characterizing one or more pathogens in a sample comprising:
    obtaining a medical device which has made physical contact with the sample;
    forming or placing a Surface Enhanced Raman Scattering (SERS) sensor on the medical device after it has been used on or in a patient; and
    analyzing the SERS sensor with Raman spectroscopy or microscopy.

2. The method of claim 1 wherein the SERS sensor is deposited or otherwise placed inside a biofilm formed on the surface of the medical device.

3. The method of claim 1 wherein the SERS sensor is deposited or otherwise placed where a biofilm is suspected to have formed on the surface of the medical device.

4. The method of claim 1 wherein analyzing comprises detecting the presence of one or more biomarkers for the one or more pathogens.

5. The method of claim 4 wherein the one or more biomarkers are metabolic products of the one or more pathogens.

6. The method of claim 4 wherein the one or more biomarkers are associated with a pathogen that is drug resistant.

7. The method of claim 1 wherein the sample is a fluid or tissue sample taken from a patient.

8. An implanted medical device having a surface and a SERS sensor on at least a portion of the surface.

9. The medical device of claim 8 wherein the medical device is a catheter.

* * * * *